United States Patent [19]

Terada et al.

[11] 4,335,213
[45] Jun. 15, 1982

[54] PROCESS FOR THE PREPARATION OF GALACTOSE OXIDASE

[75] Inventors: Osamu Terada; Kazuo Aisaka, both of Machida, Japan

[73] Assignee: Kyowa Hakko Kogyo Co., Ltd., Tokyo, Japan

[21] Appl. No.: 164,523

[22] Filed: Jul. 2, 1980

[30] Foreign Application Priority Data

Jul. 5, 1979 [JP] Japan .................................. 54-84407

[51] Int. Cl.³ .............................................. C12N 9/04
[52] U.S. Cl. ..................................... 435/190; 435/911
[58] Field of Search ................................ 435/190, 911

[56] References Cited

U.S. PATENT DOCUMENTS 3,186,921  6/1965  Rupe et al. ........................ 435/190

OTHER PUBLICATIONS

Gancedo et al., "Widespread Occurrence of Galactose Oxidase and Glycose Oxidase in Fungi" in Archives, Biochem. & Biophysics, vol. 119, pp. 588-590.

*Primary Examiner*—Lionel M. Shapiro
*Attorney, Agent, or Firm*—Fitzpatrick, Cella, Harper & Scinto

[57] ABSTRACT

Galactose oxidase is produced by culturing a microorganism belonging to the genus Gibberella. The enzyme is useful in the determination of galactose.

6 Claims, No Drawings

PROCESS FOR THE PREPARATION OF GALACTOSE OXIDASE

BACKGROUND OF THE INVENTION

The present invention pertains to a process for the preparation of the enzyme galactose oxidase; and more specifically, to a process for the preparation of galactose oxidase by culturing a microorganism belonging to the genus Gibberella.

Galactose oxidase (EC 1.1.3.9) is useful for the determination of galactose in organisms and biological fluids such as serum. Heretofore, it has been known that galactose oxidase can be produced by a microorganism belonging to the species *Polyporus circinatus* [J. A. D. Cooper et al.; J. Biol. Chem., 234, 445 (1959), Japanese Examined Patent Application No. 5900/1966, etc.]. However, other efficient sources of the enzyme are desirable and in demand. To this end, it has now been found that galactose oxidase may be produced in high yield by culturing microorganisms of the genus Gibberella.

SUMMARY OF THE INVENTION

In accordance with the present invention, galactose oxidase is produced by culturing a microorganism belonging to the genus Gibberella which is capable of producing said enzyme in a nutrient medium until substantial enzymatic activity is detected in the culture liquor and thereafter separating said enzyme from the culture liquor. The process of the invention attains production of the enzyme in high yield in the culture liquor and particularly in the cell-free culture liquor. The galactose oxidase produced by the process herein disclosed acts upon galactose, one of the monosaccharides as well as such polysaccharides as melibiose.

DETAILED DESCRIPTION OF THE INVENTION

Organisms useful for carrying out the process of the present invention belong to the genus Gibberella. Within this genus, organisms of the species *Gibberella fujikuroi* and *Gibberella zeae* are preferred and particularly preferred strains are *Gibberella fujikuroi* Y-530929 (FERM-P No. 5,066) (NRRL 12168), *Gibberella fujikuroi* T-280530 (FERM-P No. 5,067) (NRRL 12169) and *Gibberella zeae* K-240319 (FERM-P No. 5,068). However, it should be understood that any microorganism belonging to the genus Gibberella which has the ability to produce the desired enzyme is suitable for the present invention.

The microbiological properties of the species *Gibberella fujikuroi* and *Gibberella zeae* are described in the Dictionary of the Fungi, 6th Ed., page 241 (1971).

As the medium for culturing the above strains, either a natural medium or a synthetic medium may be used as long as it contains suitable carbon sources, nitrogen sources, inorganic materials and other nutrients.

As carbon sources, carbohydrates such as galactose, glucose, fructose, sucrose, maltose, mannose, melibiose, raffinose starch, starch hydrolyzate liquor, molasses, etc.; sugar alcohols such as glycerol, sorbitol, mannitol, etc.; organic acids such as acetic acid, lactic acid, pyruvic acid, fumaric acid, citric acid, etc.; alcohols such as methanol, ethanol, etc.; glycols such as ethylene glycol, propylene glycol, etc.; amino acids; and hydrocarbons such as n-hexadecane, etc. may be used. Galactose, glycerol, fructose, sucrose, glucose, melibiose and raffinose are preferred for increasing the yield of the desired enzyme.

As nitrogen sources, ammonia; inorganic and organic ammonium salts such as ammonium chloride, ammonium carbonate, ammonium phosphate, ammonium nitrate, ammonium acetate, etc.; nitrogen-containing compounds such as urea, amino acids, etc.; nitrogenous organic materials such as peptone, NZ-amine (trademark for enzymatic hydrolyzate of casein available from Sheffield Chemical Co., United States), meat extract, yeast extract, soluble vegetable protein, corn steep liquor, casein hydrolyzate, chrysalis hydrolyzate, fish meal or its digested product, defatted soybean or its digested product, and the like are appropriate. Meat extract, yeast extract and soluble vegetable protein are preferred for increasing the yield of the enzyme.

As inorganic materials, potassium dihydrogen phosphate, dipotassium hydrogen phosphate, potassium chloride, magnesium sulfate, manganese sulfate, ferrous sulfate, sodium chloride, calcium carbonate and the like are appropriate.

We have found that the yield of galactose oxidase can be greatly enhanced in the presence of zinc ion or copper ion in the culture medium. Zinc compounds such as zinc chloride, zinc sulfate, and the like are used as compounds offering zinc ion. Copper compounds such as copper sulfate, cupric chloride and the like are used as compounds offering copper ion. Good results are obtained by adding a zinc compound in an amount of 0.0001–0.005% (w/v) or a copper compound in an amount of 0.001 to 0.05% (w/v) to the medium. Culturing is carried out with aeration and stirring at 25°–35° C. and at a pH of 6.0–7.0 for 2–3 days.

Isolation and purification of galactose oxidase from the culture liquor is carried out according to the conventional methods, the following being exemplary.

The culture liquor is filtered or centrifuged to remove the microbial cells and the resultant filtrate or supernatant is concentrated to about one-fourth of its original volume under reduced pressure.

Ammonium sulfate is added to the concentrate to 60% saturation to form a precipitate. The precipitate is recovered and dissolved in 0.01 M phosphate buffer (pH 7.0), and the solution is dialyzed for desalting. The dialyzate is subjected to DEAE - cellulose column chromatography and Sephadex G-150 (Sephadex is trademark for molecular sieve, derivatives of dextran, available from Pharmacia Fine Chemicals Inc., U.S.A.) column chromatography. The resulting purified enzyme solution is freeze-dried to obtain galactose oxidase in powdered form.

The properties of galactose oxidase produced by *Gibberella fujikuroi* Y-530929 are described below. Galactose oxidases produced by *Gibberella fujijuroi* T-280530 and *Gibberella zeae* K-240319 have essentially the same properties.

The enzyme activity of the galactose oxidase is assayed by converting galactose in the presence of galactose oxidase and oxygen to galactohexodialdose and hydrogen peroxide, reacting the hydrogen peroxide with 4-aminoantipyrine and phenol in the presence of peroxidase to form a quinoneimine hereinafter described, and then determining the quinoneimine thus produced. The reaction process is illustrated by the following reaction formula (1) and (2).

$$\text{galactose} + O_2 \xrightarrow{\text{galactose oxidase}} \text{galactohexodialdose} + H_2O_2 \quad (1)$$

$$2H_2O_2 + \text{4-aminoantipyrine} + \text{phenol} \xrightarrow{\text{peroxidase}} \text{quinoneimine} + 4H_2O \quad (2)$$

The reaction formula (2) and determination of hydrogen peroxide utilizing the reaction are illustrated in C.C. Allain et al., Clin. Chem., 20, 470 (1974).

The operative steps for the determination of galactose using galactose oxidase and a method for calculation of the enzyme potency are described below.

(A) Reagent

| (1) | substrate: | 0.5M aqueous solution of galactose | 0.5 ml |
|---|---|---|---|
| (2) | buffer: | 0.25M phosphate buffer (pH 7) | 1.0 ml |
| (3) | 4-aminoantipyrine: | 24 mM aqueous solution | 0.5 ml |
| (4) | phenol: | 42 mM aqueous solution | 0.5 ml |
| (5) | aqueous solution of peroxidase: | (protein 2 mg/ml, specific activity 100) | 0.1 ml |
| (6) | water | | 0.3 ml |
| (7) | enzyme solution | (an aqueous solution of galactose oxidase) | 0.1 ml |

(B) Operation

The above reagents (1)–(6) are placed in a test tube and the tube is shaken at 25° C. for 5 minutes. Then the mixture is made up to 3 ml with the enzyme solution (7). Reaction is carried out with shaking at 25° C for 10 minutes. The same procedure as that described above is repeated except that water is used as a control in place of the substrate. Absorbencies of the reaction solution and the control at 500 nm are measured respectively. The difference in the absorbencies is expressed by $\Delta OD$.

(C) Calculating method of potency

One unit of galactose oxidase is the amount of the enzyme which decomposes 1 μmole of galactose at 25° C. in one minute.

The absorption coefficient of 1 mM of the quinoneimine is 5.33 [Clin. Chem. 20, 470 (1974)]. Absorbency ($\Delta OD$) of 3 ml of the reaction solution at 500 nm calculated according to the operation (B) is symbolized by "a". Then, potency (A) of 1 ml of the enzyme solution is calculated using the following formula.

$$A = a \times \frac{1}{5.33} \times 3 \times \frac{1}{10}$$

$$= a \times 0.056 \text{ (unit/ml)}$$

Various properties of the galactose oxidase obtained in the present invention are illustrated below.

(1) Action

Galactose is oxidized in the presence of the present enzyme and oxygen to produce hydrogen peroxide and galactohexodialdose.

(2) Substrate specificity

The present enzyme is specific to galactose and also acts on melibiose, raffinose, dihydroxyacetone, and the like but not on glucose, glycerol, etc. as is illustrated in the following table.

| Substrate | Relative activity (%) |
|---|---|
| galactose | 100 |
| galactonolactone | 5 |
| galacturonic acid | 0 |
| glucose | 0 |
| mannose | 0 |
| fructose | 4 |
| rhamnose | 1 |
| inositol | 0 |
| xylose | 0 |
| lactose | 1 |
| melibiose | 68 |
| raffinose | 98 |
| glycerol | 1 |
| dihydroxyacetone | 135 |

(3) Optimum pH

The optimum pH of the present enzyme is around 6.0~7.0 in the reaction at 25° C. for 10 minutes.

(4) Stable pH range

The stable pH range is 5.0~8.0 in the reaction at 45° C. for 15 minutes.

(5) Optimum temperature range

The optimum temperature is around 20°~30° C. in the reaction at pH 7.0 for 10 minutes.

(6) Heat stability

The enzyme is stable up to 50° C. when treated at pH 7.0 for 15 minutes and loses about 90% of its activity at 60° C.

(7) Inhibitor

The enzyme is inhibited by the following substances in the reaction of 25° C. and pH 7.0.

| Inhibitor | Concentration (M) | Inhibition rate (%) |
| --- | --- | --- |
| AgNO$_3$ | $10^{-4}$ | 100 |
| NaN$_3$ | $10^{-3}$ | 94 |
| PCMB* | $10^{-3}$ | 57 |
| NH$_2$OH | $10^{-4}$ | 100 |
| EDTA** | $10^{-3}$ | 52 |
| o-phenanthroline | $10^{-3}$ | 68 |
| DDC*** | $10^{-5}$ | 69.3 |
| DDC*** | $10^{-4}$ | 84.8 |
| DDC*** | $10^{-3}$ | 100 |

*PCMB : parachloromercurybenzoate
**EDTA : ethylenediaminetetraacetic acid
***DDC : diethyldithiocarbamate, a chelator which specifically acts on copper ion (8) Molecular weight Molecular weight of the enzyme is determined to be about 45,000 according to the gel-filtration method using Sephadex G 75.

(9) Analysis of metal

The enzyme contains about 1 g atom of copper per mole. The analysis is made by atomic absorption spectrometry using an apparatus for atomic absorption spectrometry such as a type AA-1 available from Nippon Denshi Co., Ltd.

Certain specific embodiments of the present invention are illustrated by the following representatives examples.

EXAMPLE 1

In this example, Gibberella fujikuroi Y-530929 (NRRL 12168) is inoculated into 300 ml of a medium (pH 6.0) comprising 1 g/dl galactose, 1 g/dl soluble vegetable protein, and 0.001 g/dl ZnCl$_2$ in a 2 l-Elrenmeyer flask and cultured with shaking at 30° C. for 48 hours.

Then, 600 ml of culture liquor obtained as in the above step is transferred to a 30 l-jar fermenter containing 15 l of culture medium having the same composition as in the above step. Culturing is carried out with aeration of 15 l/minute and stirring at 300 r.p.m. at 30° C. for 48 hours.

Thereafter, the entire culture liquor is filtered through a large Buchner funnel.

The filtrate is concentrated under reduced pressure until the volume is about one-fourth. Ammonium sulfate is added to the concentrate and the precipitate which is deposited with 90% saturation of ammonium sulfate are recovered.

The yield in terms of activity of galactose oxidase contained in the precipitate is about 70% and the specific activity is elevated to about threefold.

The precipitate is dissolved in a small amount (about 100 ml) of 0.01 M phosphate buffer (pH 7.0). This solution is dialyzed against 10 l of the same buffer for 24 hours. The dialyzate is charged onto a column (6 cm in diameter) packed with 1 l of DEAE-cellulose equilibrated with the same buffer. Galactose oxidase passes through without being adsorbed on the DEAE-cellulose. The effluent is taken in fractions. The active fractions are combined and ammonium sulfate is added. The precipitate which is deposited with 90% saturation of ammonium sulfate is collected by centrifugation (12,000×g, 20 minutes) and dissolved in 10 ml of 0.01 M phosphate buffer (pH 7.0). The solution is dialyzed against 5 l of the same buffer for 24 hours.

After dialysis the enzyme solution is charged onto a column (3.5 cm in diameter) packed with 500 ml of Sephadex G-150 equilibrated in advance with the same buffer. The effluent is taken in fractions. The active fractions are collected and freeze-dried whereby 25 mg of purified galactose oxidase preparate exhibiting a specific activity of 13 units/mg is obtained as a powder.

The specific activity of the purified enzyme is elevated 100 times as much as that of the cell filtrate and the yield in terms of activity is 50%.

EXAMPLE 2

In this example, the same procedure as in Example 1 is repeated except that Gibberella fujikuroi T-280530 (NRRL 12169) and a fermentation medium (pH 6.0) comprising 1 g/dl sucrose, 1 g/dl soluble vegetable protein and 0.001 g/dl ZnCl$_2$ are used. As a result, about 20 mg of purified galactose oxidase having a specific activity of 10 units/mg is obtained. The yield in terms of activity is 45%.

EXAMPLE 3

In this example, the same procedure as in Example 2 is repeated except that Gibberella zeae K-240319 ((FERM-P No. 5,068) is used to obtain about 20 mg of purified galactose oxidase having a specific activity of 8 units/mg. The yield in terms of activity is 40%.

EXAMPLE 4

In this example, the same procedure as in Example 1 is repeated except that a medium (pH 6.0) comprising 1 g/dl galactose, 1 g/dl yeast extract, and 0.01 g/dl CuSO$_4$.5 H$_2$O is used to obtain about 20 mg of purified galactose oxidase having a specific activity of 12 units/mg. The yield in terms of activity is 50%.

About 2 mg of purified galactose oxidase having a specific activity of 11 units/mg is obtained when the same procedure as above is repeated except that a medium (pH 6.0) comprising 1 g/dl galactose and 1 g/dl yeast extract is used.

What is claimed is:

1. A process for producing galactose oxidase which comprises culturing a microorganism belonging to the species Gibberella fujikuroi or Gibberella zeae which is capable of producing said enzyme in a nutrient medium, until substantial enzymatic activity is detected in the culture liquor, and thereafter recovering said enzyme from the culture liquor.

2. A process according to claim 1 wherein said microorganism is selected from the group consisting of Gibberella fujikuroi Y-530929 (NRRL 12168), Gibberella fujikuroi T-280530 (NRRL 12169), and Gibberella zeae K-240319, (FERM-P No. 5,068).

3. A process according to claim 1 wherein said culturing step is carried out in the presence of zinc ion.

4. A process according to claim 1 wherein said culturing step is carried out in the presence of copper ion.

5. A process according to claim 3 wherein said zinc ion is supplied by adding from 0.0001 to 0.005% (w/v) of a compound selected from the group consisting of zinc chloride and zinc sulfate to said culture medium.

6. A process according to claim 4 wherein said copper ion is supplied by adding from 0.001 to 0.05% (w/v) of a compound selected from the group consisting of copper sulfate and cupric chloride to said culture medium.

* * * * *